US00PP36894P2

(12) United States Plant Patent
Bourne

(10) Patent No.: US PP36,894 P2
(45) Date of Patent: Aug. 19, 2025

(54) GRAPEVINE NAMED 'SV36-25-451'

(50) Latin Name: *Vitis vinifera L.*
Varietal Denomination: SV36-25-451

(71) Applicant: Sunview Vineyards of California, Inc., Delano, CA (US)

(72) Inventor: Timothy F Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 18/831,201

(22) Filed: Sep. 10, 2024

(51) Int. Cl.
*A01H 5/08* (2018.01)
*A01H 6/88* (2018.01)

(52) U.S. Cl.
USPC ..... Plt./207

(58) Field of Classification Search
USPC ..... Plt./205, 207
See application file for complete search history.

(56) References Cited

U.S. PATENT DOCUMENTS

PP28,270 P3 * 8/2017 Sheehan ..... A01H 5/08
Plt./207

* cited by examiner

*Primary Examiner* — Susan McCormick Ewoldt
(74) *Attorney, Agent, or Firm* — Eric C. Cole; Baker Manock & Jensen, PC

(57) ABSTRACT

A new and distinct variety of grapevine plant named 'SV36-25-451' particularly characterized by its large, yellow green skinned berries with crisp flesh and muscat flavor and which ripen in late July in the McFarland, California area.

4 Drawing Sheets

Latin name of the genus and species of the plant claimed: The plant claimed relates to a new and distinct variety of *Vitis vinifera L.*

Variety denomination: The plant claimed shall be known as 'SV36-25-451'.

BACKGROUND OF THE INVENTION

The present invention relates a new and distinct cultivar of grapevine botanically known as *Vitis vinifera* and hereinafter referred to as grapevine named 'SV36-25-451'. As used herein, 'grapevine' refers to all plant parts including, vines, canes, tendrils, leaves, fruit and roots of 'SV36-25-451'. Grapevine named 'SV36-25-451' is the result of an effort to produce a mid-season green grape with excellent fruit characteristics. This new cultivar originated from a cross conducted in May 2015 near McFarland, California between female grapevine plant selection 'SV17-55-220' (unpatented) and male grapevine plant 'SV21-66-226' (U.S. Plant Pat. No. 24,531). Resultant ovules from the cross were harvested 42 days after pollination and cultured on 'McCown's Woody Plant Medium'. Subsequently, the resultant embryonic plants were cultured in the same medium in the laboratory under twelve hours of light from LED lamps at 29° C. The seedlings from this effort were transplanted to the greenhouse in November of 2015 and grown in the greenhouse at 29° C. with 12 hours illumination under LED lamps. The seedling population of 140 plants was planted in the field in the spring of 2016 near McFarland, California. The new grapevine was selected from this seedling population on Sep. 12, 2018. It was then propagated by cuttings and grafted to 'Freedom' (unpatented) rootstock in 2019. The present invention has been found to retain its distinctive characteristics through two successive asexual propagations.

Grapevine named 'SV36-25-451' differs from its female parent grapevine 'SV17-55-220' in that 'SV36-25-451' has large, elliptical shaped, yellow green seedless berries and flowers with functional pollen, whereas 'SV17-55-220' has medium sized, elliptical shaped, green seedless berries and flowers that are pistillate.

Grapevine named 'SV36-25-451' differs from its male parent 'SV21-66-226' in that 'SV36-25-451' has berries are elliptical shaped whereas 'SV21-66-226' has ovate shaped berries.

Grapevine named 'SV36-25-451' most closely resembles commercially available grapevine named 'Sheegene 17' (U.S. Plant Pat. No. 28,270) but 'SV36-25-451' has berries with a mild, muscat flavor whereas 'Sheegene 17' (U.S. Plant Pat. No. 28,270) has berries with a sweet, neutral flavor.

SUMMARY OF THE INVENTION

The following are the most outstanding and distinguishing characteristics of the ripe fruit of this new variety when grown under normal horticultural practices near McFarland, California:

a. Yellow green berries.
b. Crisp berry texture; and
c. Large, muscat-flavored berries.

BRIEF DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures. The photographs were taken from the seedling vine and from a plant about 4 years-old, grown in a field near McFarland, California in 2022.

DETAILED BOTANICAL DESCRIPTION

Figure 1:
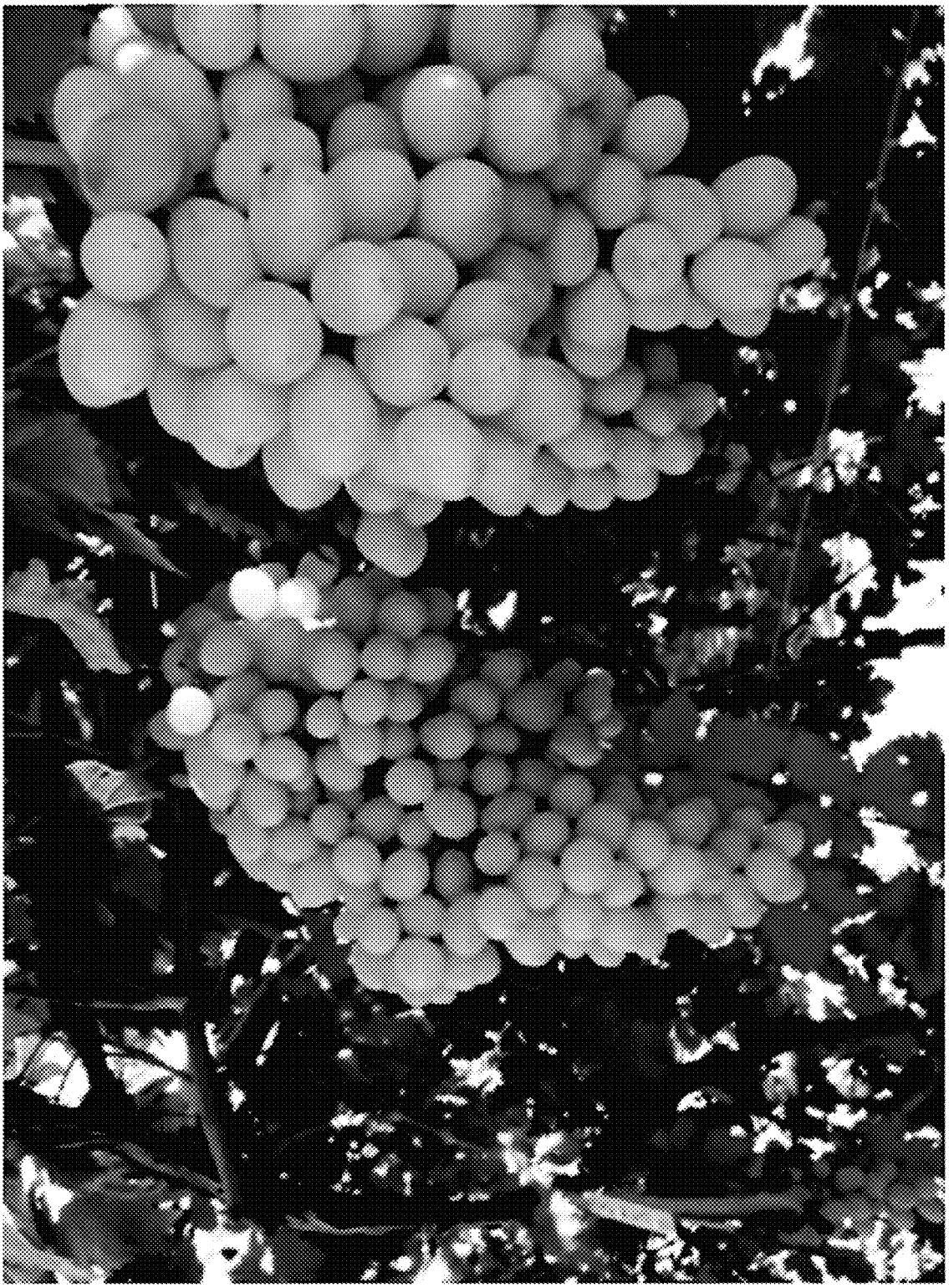
FIG. 1 Fruit clusters on the seedling vine.
Figure 2:
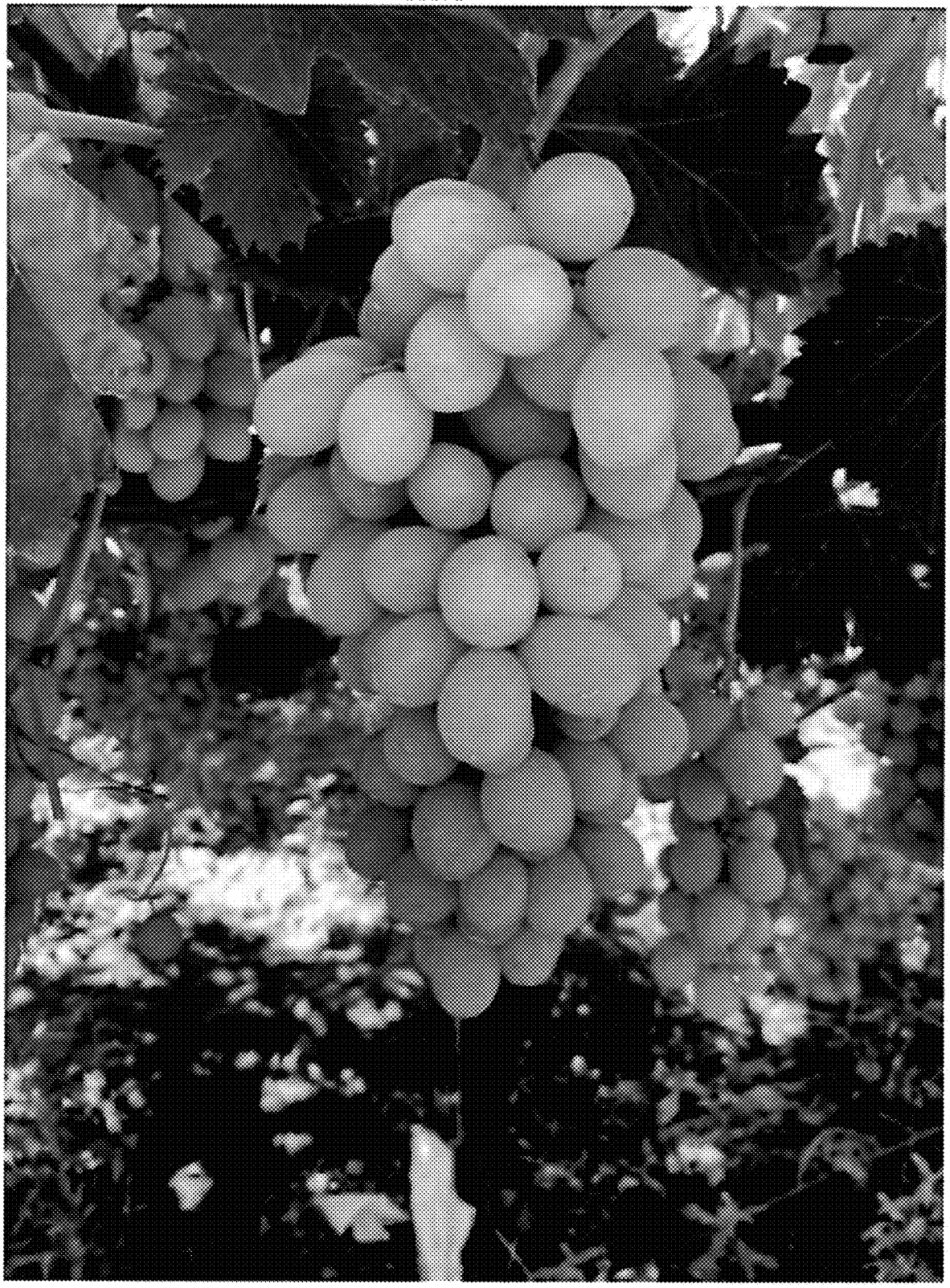
FIG. 2 Fruit cluster on vine treated with exogenous gibberellic acid and trunk girdling.
Figure 3:
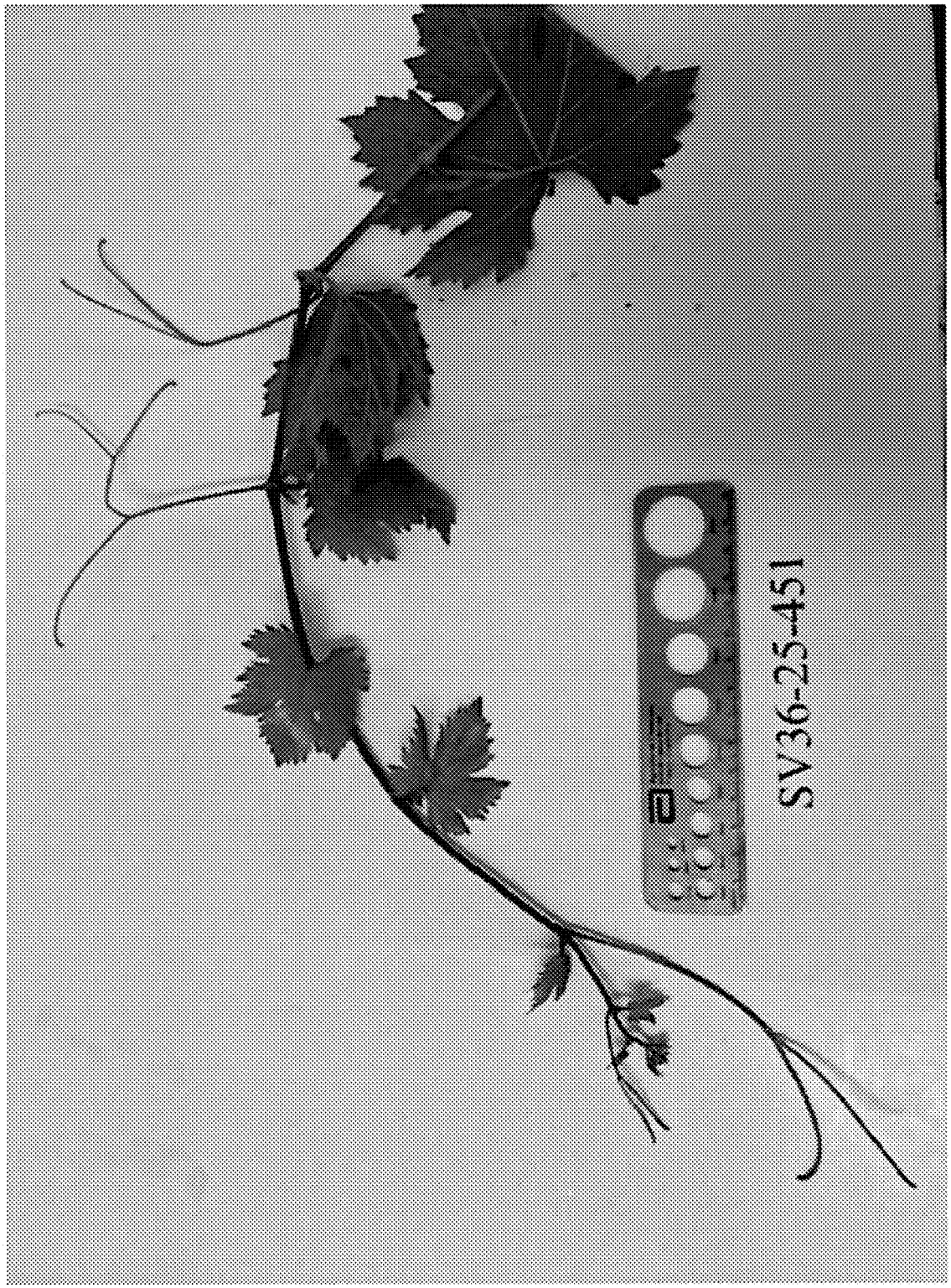
FIG. 3 Shoots, leaves, and tendrils on young shoot.
Figure 4:
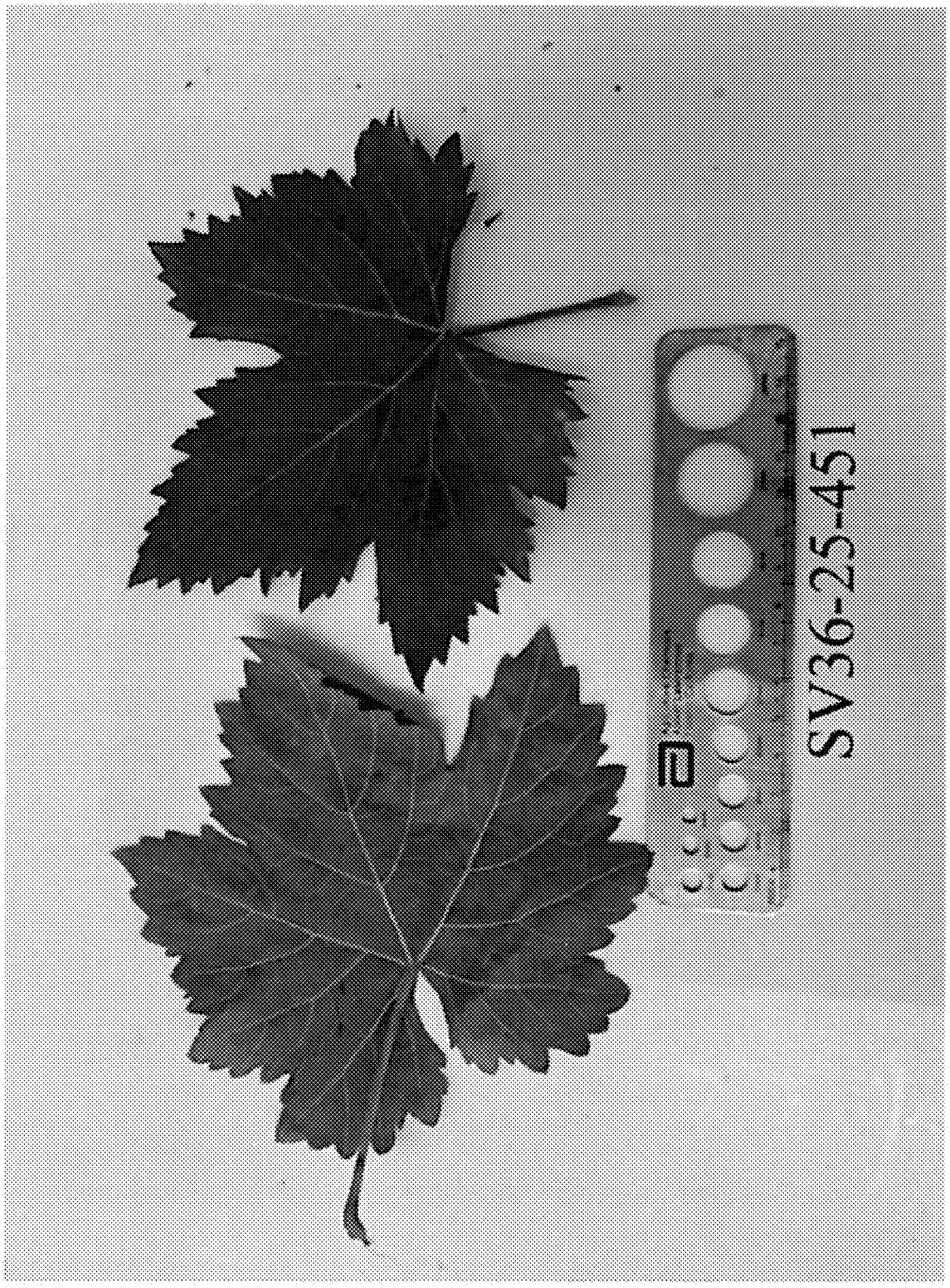
FIG. 4 Mature leaves, upper and lower surfaces.

The following detailed description sets forth the distinctive characteristics of 'SV36-25-451'. Descriptions of the new invention apply to vines of 'SV36-25-451' grown on 'Freedom' rootstock at a density of 1,537 vines per hectare grown near McFarland, California in 2022. These vines were in their fourth year of production, having been planted in 2019. These descriptions are believed to apply generally to the new variety grown under similar circumstances elsewhere. Color references are primarily to The Royal Horticultural Society's Colour Chart, The Royal Horticultural Society, London, United Kingdom. Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in Descriptors for Grapevine (*Vitis* spp.) (Anonymous, International Plant Genetic Resources Institute, 1997, ISBN 92-9043-352-3).

Classification:

*Family*.—Vitaceae.

*Botanical name*.—*Vitis vinifera*.

*Variety name*.—'SV36-25-451'.

Plant:

*Vigor*.—Very vigorous. Vines spur-pruned and shoot thinned to 32 shoots average 343 cm of growth per cane.

*Density of foliage*.—Moderate.

*Productivity*.—Very productive when spur pruned, up to 38,000 kg/hectare.

*Hardiness*.—Hardiness observed to 0° C.

*Rootstock*.—'Freedom' (unpatented).

Trunk:

*Shape*.—Broadly elliptic.

*Straps*.—Long, split.

*Surface texture*.—Shaggy.

*Trunk circumference*.—21.6 cm at 1.0 m of height.

*Inner bark color*.—RHS Greyed Orange group N170C.

*Outer bark color*.—RHS Greyed group 201A.

Mature leaves:

*Average blade length*.—17.3 cm.

*Average blade width*.—20.7 cm.

*Size of blade*.—Large.

*Shape*.—Pentagonal.

*Number of lobes*.—5.

*Anthocyanin coloration of main veins on the upper side of the blade*.—Absent.

*Mature leaf profile*.—Undulating.

*Blistering (upper surface)*.—Absent.

*Leaf blade tip*.—Curved downward.

*Margins*.—Lobed, serrated, undulating.

*Apex*.—Broadly acuminate.

*Bases*.—Sagittate.

*Thickness*.—Medium.

*Undulation of blade between main and lateral veins*.—Slight.

*Shape of teeth*.—Mix of straight edged and convex.

*Length of teeth*.—About 9.2 mm.

*Width of teeth*.—About 10.3 mm.

*Ratio length/width of teeth*.—About 1:1.

*General shape of petiole sinus*.—Wide open.

*Tooth at petiole sinus*.—Absent.

*Petiole sinus limited by veins*.—Absent.

*Shape of upper lateral sinus*.—Slightly open.

*Depth of upper lateral sinus*.—Shallow.

*Prostrate hairs between veins (lower surface)*.—Absent.

*Erect hairs between veins (lower surface)*.—Absent.

*Prostrate hairs on main veins (lower surface)*.—Absent.

*Density of erect hairs on main veins (lower surface)*.—Medium.

*Prostrate hairs on main veins (upper surface)*.—Absent.

*Erect hairs on main veins (upper surface)*.—Sparse; limited to junctions of main veins.

*Upper surface*.—Summer color: RHS Yellow Green group 147A. Surface texture: Smooth. Surface appearance: Dull. Goffering of blade: Absent.

*Lower surface*.—Summer color: RHS Yellow Green group 147B. Anthocyanin coloration of main veins on lower leaf surface: Absent. Glossiness: Medium. Pubescence distal portion of surface: Absent. Surface texture: Rough. Surface appearance: Slightly glossy.

*Petiole*.—Length: 15.0 cm. Length of petiole compared to middle vein: About equal. Density of prostrate hairs: Absent. Density of erect hairs: Absent. Shape of base of petiole sinus: Wide open. Color: In shade: RHS Yellow Green group 145B. In sun: RHS Yellow Green group 144C.

Tendrils:

*Number*.—Bifurcated and trifurcated; forming irregularly at node 5 and above.

*Length*.—22.6 cm.

*Diameter*.—2.3 mm.

*Texture*.—Smooth.

*Color*.—RHS Yellow Green group N144B.

Growing tips (young shoots):

*Pubescence*.—Abundant, prostrate.

*Color*.—RHS Yellow Green group 144A.

*Anthocyanins*.—Absent.

*Shape*.—Rounded.

*Apex*.—Fully open.

*Prostrate hair on tips*.—Present.

*Anthocyanin on prostrate hair*.—Absent.

*Erect hairs on tips*.—Absent.

*Shoot attitude*.—Erect.

Green summer shoots:

*Internode color upper surface*.—RHS Yellow Green group 152A.

*Internode color lower surface*.—RHS Yellow Green group 144A.

*Node color upper surface*.—RHS Yellow Green group 148A.

*Node color lower surface*.—RHS Yellow Green group 143B.

*Density of erect hairs on internodes*.—Absent.

Woody shoot:

*Canes*.—Shape: Elliptic. Internode length: 8.8 cm. Width at node: 15.3 mm. Surface: Smooth. Main color: Greyed Orange group 166C. Lenticels: Inconspicuous.

*Buds*.—Shape: Rounded Cane bud fruitfulness: Highly fruitful from basal buds, each shoot producing one or two flower clusters. Length: 4.5 mm. Width: 3 mm. Height: 3 mm. Color: Greyed orange group 166A.

Flowers:

*Flower sex*.—Perfect.

*Position of first flowering nodes*.—3rd, 4th or 5th node.

*Number of inflorescences per shoot*.—1 or 2.

*Flower cluster width*.—5.7 cm.

*Flower cluster length*.—24.3 cm.

*Cluster stem color*.—RHS Yellow green group 144B.

*Calyptra color*.—RHS Yellow green group 144A.

*Ovary length*.—2 mm.

*Ovary width*.—1 mm.

*Ovary color*.—RHS Green group 143B.

*Filament length*.—2 mm.

*Filament color*.—RHS Yellow green group 145D.

*Anther length*.—1 mm

*Anther color*.—Yellow group 8C.

*Date of full bloom*.—May 10, 2022.

Fruit:

*Ripening period*.—Early mid-season, McFarland, California.

*Date of ripening*.—Jul. 26, 2022, McFarland, California.

*Use*.—Fresh market.

*Keeping quality*.—Very good.

*Shipping quality*.—Good.

*Date of first harvest*.—Jul. 27, 2022.

*Solids-sugar*.—High.

*Refractometer test*.—20.5 brix.

*Titratable acidity*.—0.4 2g/liter.

*pH*.—3.5.

*Bunch*.—Size: Medium. Length (peduncle excluded): About 21.0 cm. Width: About 17.0 cm. Weight: Natural, without gibberellic acid treatment: 425 g. With gibberellic acid treatment: 940 g. Density: Loose, well filled. Number of berries: 89. Form: Conical.

*Peduncle*.—Length: About 7.9 cm. Lignification: 0.3 cm of peduncle. Color: RHS Yellow Green group 144B.

*Berry*.—Size: Large. Uniformity of size: Uniform. Weight: Natural, without gibberellic acid treatment: 4.7 g. With gibberellic acid treatment: 9.1 g. Shape: Natural, without gibberellic acid treatment: Elliptic. With gibberellic acid treatment: Elliptic. Presence of seeds: Seedless; most berries develop one or two small, partially lignified rudimentary seeds less than 1.0 mm in length. Cross section: Circular. Dimensions: Natural: Longitudinal axis: 2.4 cm. Natural: Horizontal axis: About 1.8 cm. With gibberellic acid treatment, longitudinal axis: 3.4 cm. With gibberellic acid treatment, horizontal axis: 2.3 cm. Skin color (without bloom): RHS Yellow green group 144C. Coloration of flesh: RHS Yellow green group 145D. Juiciness of flesh: Slightly juicy. Berry firmness: Firm. Particular flavor: Light muscat. Bloom (cuticular wax): Medium. Pedicel length: 0.9 cm. Berry separation from pedicel: Slightly difficulty.

*Skin*.—Thickness: Medium. Texture: Crisp. Reticulation: Absent. Roughness: Absent. Tenacity: Tenacious to flesh. Tendency to crack: Resistant.

Disease and insect resistance: No particular resistance or susceptibility has been observed. Normal disease control practices can be used.

I claim:

1. A new and distinct variety of grapevine plant named 'SV36-25-451', substantially as illustrated and described herein.

* * * * *